United States Patent
Kinreich

(10) Patent No.: US 11,589,796 B2
(45) Date of Patent: Feb. 28, 2023

(54) METHOD AND SYSTEM FOR ANALYZING NEURAL AND MUSCLE ACTIVITY IN A SUBJECT'S HEAD FOR THE DETECTION OF MASTICATION

(71) Applicant: Sivan Kinreich, Tel Aviv (IL)

(72) Inventor: Sivan Kinreich, Tel Aviv (IL)

( * ) Notice: Subject to any disclaimer, the term of this patent is extended or adjusted under 35 U.S.C. 154(b) by 460 days.

(21) Appl. No.: 16/484,210

(22) PCT Filed: Jan. 31, 2018

(86) PCT No.: PCT/IL2018/050106
§ 371 (c)(1),
(2) Date: Aug. 7, 2019

(87) PCT Pub. No.: WO2018/146672
PCT Pub. Date: Aug. 16, 2018

(65) Prior Publication Data
US 2020/0015697 A1    Jan. 16, 2020

Related U.S. Application Data

(60) Provisional application No. 62/456,704, filed on Feb. 9, 2017.

(51) Int. Cl.
*A61B 5/375*     (2021.01)
*A61B 5/369*     (2021.01)
(Continued)

(52) U.S. Cl.
CPC ............ *A61B 5/375* (2021.01); *A61B 5/0006* (2013.01); *A61B 5/369* (2021.01); *A61B 5/389* (2021.01);
(Continued)

(58) Field of Classification Search
CPC ......... A61B 5/375; A61B 5/369; A61B 5/389; A61B 5/0006; A61B 5/4542;
(Continued)

(56) References Cited

U.S. PATENT DOCUMENTS

| 4,355,645 A | 10/1982 | Mitani et al. |
| 2011/0125063 A1 | 5/2011 | Shalon et al. |

(Continued)

FOREIGN PATENT DOCUMENTS

| CN | 107049327 | 8/2017 |
| JP | 2002-253520 | 9/2002 |

(Continued)

OTHER PUBLICATIONS

International Search Report for PCT/IL2018/050106 dated May 30, 2018, 2 pages.

(Continued)

*Primary Examiner* — Patrick Fernandes
*Assistant Examiner* — Liam A Wallace
(74) *Attorney, Agent, or Firm* — Nixon & Vanderhye PC

(57) ABSTRACT

The present invention relates to a method and system for calculating eating bites of a user. The method comprises: (a) continuously measuring the electrical properties data of mastication of a user for a predetermined period of time; (b) periodically determining single eating bites according to the data obtained in step (a) through a time interval; (c) periodically storing the bites determined throughout the predetermined period of time, through a time interval.

4 Claims, 8 Drawing Sheets

(51) Int. Cl.
　　*A61B 5/389*　　(2021.01)
　　*A61B 5/00*　　(2006.01)
(52) U.S. Cl.
　　CPC .......... *A61B 5/4542* (2013.01); *A61B 5/6814* (2013.01); *A61B 5/7203* (2013.01); *A61B 5/7257* (2013.01); *A61B 5/7405* (2013.01); *A61B 5/746* (2013.01); *A61B 2562/046* (2013.01)
(58) Field of Classification Search
　　CPC ... A61B 5/6814; A61B 5/7203; A61B 5/7257; A61B 5/7405; A61B 5/746; A61B 2562/046
　　See application file for complete search history.

(56) References Cited

U.S. PATENT DOCUMENTS

| | | | | |
|---|---|---|---|---|
| 2014/0275748 | A1* | 9/2014 | Utard | A61B 5/0537 604/66 |
| 2015/0313496 | A1 | 11/2015 | Connor | |
| 2016/0073953 | A1* | 3/2016 | Sazonov | A61B 5/1107 600/590 |

FOREIGN PATENT DOCUMENTS

| | | | | |
|---|---|---|---|---|
| JP | 2012-005664 | | 1/2012 | |
| JP | 2014533589 | A * | 12/2014 | ............. A61B 5/742 |
| WO | WO-2015166739 | A1 * | 11/2015 | ........... A61B 5/4803 |

OTHER PUBLICATIONS

Written Opinion of the ISA for PCT/IL2018/050106 dated May 30, 2018, 7 pages.

Duric et al., "Neurofeedback for the treatment of children and adolescents with ADHD: a randomized and controlled clinical trial using parental reports", BMC Psychiatry, 2012, 12:107, 8 pages.

McCaig et al., "Improved modulation of rostrolateral prefrontal cortex using real-time fMRI training and meta-cognitive awareness", NeuroImage 2011, vol. 55, pp. 1298-1305.

Meisel et al., "Reprint of Neurofeedback and standard pharmacological intervention in ADHD: A randomized controlled trial with six-month follow-up", Biological Psychology, 2014, vol. 95, pp. 116-125.

* cited by examiner

METHOD AND SYSTEM FOR ANALYZING NEURAL AND MUSCLE ACTIVITY IN A SUBJECT'S HEAD FOR THE DETECTION OF MASTICATION

This application is the U.S. national phase of International Application No. PCT/IL2018/050106 filed Jan. 31, 2018 which designated the U.S. and claims the benefit of U.S. Provisional Application No. 62/456,704 filed Feb. 9, 2017, the entire contents of each of which are hereby incorporated by reference.

FIELD OF THE INVENTION

The present invention relates to the field of Neurofeedback. More particularly, the present invention relates to a system and method for detecting neural activity of eating activity (e.g. mastication, chewing, drinking, sucking, licking) in a living brain and analyzing it for intervention purposes.

BACKGROUND OF THE INVENTION

In neuroscience, different practices have been developed for detecting neural activity in a living brain. One such practice is electroencephalography (EEG), which measures electrical signals generated by the brain's neurons, via a multitude of electrodes placed on a subject's scalp. The neural signals are transmitted by wires to an EEG monitoring system that records the neural signals, and generates data about the signal variation in time, which data can be further analyzed and possibly also displayed. EEG enables high temporal resolution, in the order of milliseconds, and is therefore useful for detecting quick changes in the electrical activity of the brain.

A large percent of the western population suffer from behavioral disorders related to eating and overweight. The terms "overweight" and "obesity" refer to body weight that is greater than what is considered healthy for a certain height. Millions of people worldwide are overweight or obese. Being overweight or obese puts the individual at risk for many health problems. The more body fat that an individual has and the more the individual weighs (e.g above the defined healthy), the more likely the individual is to develop: Coronary heart disease, High blood pressure, Type 2 diabetes, Gallstones, Breathing problems and other health problems.

Overweight is a result of many factors. These factors include environment, family history and genetics, metabolism (the way the body changes food and oxygen into energy), behavior or habits, and more. Even though it is very important to keep up with healthy lifestyle habits in relation to eating, it is still somewhat of a challenge for many people. Reaching and staying at a healthy weight is a long-term challenge for people who are overweight or obese. It has been shown that physical monitoring of the body or portions thereof in real time, that includes various types of measurements applied and the analysis of the measurements can assist people in improving their health.

Many have changed their undesired habits regarding their physical activities, according to feedback received from the monitoring means. One example is the use of fitness tracking devices—like the Fitbit, Jawbone and Apple Watch which counts the individual steps of a user throughout the day. Another example is the use of Blood Glucose Monitors, like A1CNow SELFCHECK and EvenCare® G2 Glucose Meters. The real time aspect of the feedback was found to be crucial for the behavioral change in various aspects of life domains. For example, McCaig R G, Dixon M, Keramatian K, Liu I, Christoff K. "*Improved modulation of rostrolateral prefrontal cortex using real-time fMRI training and meta-cognitive awareness*", Neuroimage, 2011 Apr. 1; 55(3): 1298-305, found that participants that used a feedback application to guide their thoughts, significantly improved their ability to control their thoughts and were successfully able to perform certain mental tasks. In contrast, participants given inaccurate or no brain feedback did not achieve any improvement in brain regulation.

Another example is the growing use of EEG neurofeednack for the purpose of attention training for ADHD children and adults. In a comparison study neurofeedback was found as effective as methylphenidate medication at treating the attentional and hyperactivity symptoms of ADHD in children and adolescents (6 to 18 years). Nezla S Duric, Jorg Assmus, Doris Gundersen and Irene B Elgen, "*Neurofeedback for the treatment of children and adolescents with ADHD: a randomized and controlled clinical trial using parental reports*", BMC Psychiatry, 2012, 12:107, and "A recent randomized controlled trial with six-month follow up" by Servera Meisel, Garcia-Banda G, Cardo E, Moreno I., Reprint of "*Neurofeedback and standard pharmacological intervention in ADHD: a randomized controlled trial with six-month follow-up*", Biol Psychol. 2014 January; 95:116-25, found that immediately following neurofeedback treatment, maternal ratings for both groups (EEG neurofeedback and medication) indicated significant reductions in inattentive and hyperactive-impulsive symptoms; suggesting the EEG neurofeedback as a powerful, uninvasive promising tool to change behavior.

However, the prior art does not provide a sufficient feedback that can aid food consumption controlling.

It is therefore an object of the present invention to provide a method and means for measuring electrical signals indicating eating disorders.

It is a further object of the present invention to provide a method and means for analyzing the measured signals and providing intervention treatment accordingly in order to overcome eating disorders of a subject.

Other objects and advantages of the present invention will become apparent as the description proceeds.

SUMMARY OF THE INVENTION

The present invention relates to diagnostic techniques for detecting neural activity in a living brain, and more specifically for analyzing neural activity with the purpose of providing an individual user with a feedback about his amount and quality of chewing.

The present invention relates to a system and method for measuring, recording and analyzing neural electric signals from the user's brain or from the user's mastication muscles. Electrodes are placed either on the scalp or on or near the mastication muscles and measure the neural electric signals. The signals are transferred to a control unit (e.g. a tablet) comprising a processor and a memory. The processor in conjunction with the memory perform algorithmic calculations to the measured signals in order to detect bites and count them. If the bites exceed a predefined threshold an alert is triggered and the user is notified. Optionally, if during a predetermined time the number of bites exceed a predetermined threshold the user is also alerted. An initial pre-testing of the user in order to determine behavioral parameters (providing a behavioral baseline) may be conducted prior to the regular state measuring and used as threshold parameters during the regular state measuring.

Preferably, the present invention comprises measuring of voltage signals from the electrodes placed either on the scalp or on or near the mastication muscles; transformation of the signals to the frequency domain; extracting average PSD signals from a certain frequency band; determining if the extracted signals correspond to bites; counting the bites throughout a certain period of time and alerting the user if the counted number of bites exceed a certain threshold.

The present invention relates to measuring EEG or EMG data and perform an analysis on the measured data in order to detect a bite indicating the process of eating. The present invention further comprises analyzing the bites determined in order to alert a user if he exceeds a certain threshold.

The present invention relates to a method for calculating eating bites of a user comprising:
 (a) continuously measuring the electrical properties data of mastication of a user for a predetermined period of time;
 (b) periodically determining single eating bites according to the data obtained in step (a) through a time interval;
 (c) periodically storing the bites determined throughout the predetermined period of time, through a time interval.

Preferably, measuring the electrical properties data of mastication comprises measuring the voltage signals of EEG or EMG electrodes.

Preferably, the electrodes are placed on one or more of the following:
 i) the user's scalp;
 ii) the user's mastication muscles;
 iii) near the user's mastication muscles;
 iv) the user's neck.

Preferably, the method further comprises the following step:
 (d) periodically summing up all the number of bites stored, through a time interval.

Preferably, the method further comprises the following steps:
 (e) periodically determining if the summed up number of step (d) exceeds a predetermined threshold, through a time interval; and
 (f) triggering an alert if the determining in step (e) is deemed to be positive.

Alternatively, the method further comprises the following steps:
 (d) provided a second predetermined period of time, periodically summing up the number of bites determined during the past second predetermined period of time, through a time interval;
 (e) periodically determining if the summed up number of step (d) exceeds a predetermined threshold, through a time interval; and
 (f) triggering an alert if the determining in step (e) is deemed to be positive.

Preferably, step (d) is carried out only at certain predetermined periods of time during the day.

Alternatively, the method further comprises the following steps:
 (d) provided a second predetermined period of time, periodically summing up the number of bites during the past second predetermined period of time, every predetermined number of bites determined;
 (e) periodically determining if the summed up number of step (d) exceeds a predetermined threshold, through a time interval; and
 (f) triggering an alert if the determining in step (e) is deemed to be positive.

Preferably, the electrical properties data of mastication is one or more of the following:
 (i) the voltage signal between two pair electrodes;
 (ii) the voltage signal average of a plurality of electrode pairs;
 (iii) the voltage signal averaging of an array of electrodes.

Preferably, determining bites comprises:
 obtaining the voltage signals of mastication; transforming said voltage signals into frequency range signals;
 obtaining the PSD of a predetermined frequency band of the frequency range signals as a function of time, through time intervals;
 obtaining the PSD peaks being peaks located at maximum points of the frequency range signals in said predetermined frequency band as a function of time;
 determining the amplitudes of the PSD peaks that are above a certain threshold or within a certain range, as potential bites;
 measuring the gaps between said potential bites; determining the PSD peaks between each gap as a definite bite when the following conditions are held true in relation to each measured gap:
   (1) the measured gap is within a predetermined threshold range;
   (2) the gap's subsequent gap is within said threshold range.

Preferably, transforming the voltage signals into frequency range signals is carried out by one or more of the following:
 FFT transform;
 stockwell transform;
 Hilbert transform.

Preferably, the frequency range is the Gamma band.

Preferably, the method further comprises filtering out noises in the frequency range.

Preferably, obtaining the PSD of a predetermined frequency band of the frequency range signals as a function of time is through time intervals of 10 seconds.

Preferably, the method further comprises determining the type of food eaten according to the amplitude of the PSD peaks of the definite bites;
 wherein a type of food is determined in case a predetermined number of consecutive definite bites are within a predefined range.

Preferably, triggering an alert comprises activating a tone in earphones.

The present invention relates to a method for calculating eating bites of a user wherein the method comprises a preliminary stage carried out one or more times and a regular stage wherein:
 i. the preliminary stage comprises:
  (a) continuously measuring the electrical properties data of mastication of a user for a first predetermined period of time;
  (b) periodically determining single eating bites according to the data obtained in step (a) of the preliminary stage through a time interval;
  (c) periodically storing the bites determined throughout the first predetermined period of time, through a time interval.
  (d) periodically summing up all the number of bites stored, through a time interval;
 ii. the regular stage comprises:
  (e) continuously measuring the electrical properties data of mastication of a user for a second predetermined period of time;

(f) periodically determining single eating bites according to the data obtained in step (e) of the regular stage through a time interval;
(g) periodically storing the bites determined throughout the second predetermined period of time, through a time interval.
(h) periodically summing up all the number of bites stored, through a time interval;
(i) periodically determining if the summed up number of step (h) in the regular stage exceeds a threshold, through a time interval; and
(j) triggering an alert if the determining in step (i) of the regular stage is deemed to be positive;

wherein in case that the preliminary stage is carried out once then the threshold in the regular stage is the sum of bites determined at the end of the first predetermined period of time in the preliminary stage;

and in case that that the preliminary stage is carried out more than once then the threshold in the regular stage is an averaging, of the sums of bites determined at the end of the first predetermined period of time, of each time the preliminary stage is carried out.

The present invention relates to a method for calculating eating bites of a user wherein the method comprises a preliminary stage and a regular stage wherein:
 i. the preliminary stage comprises:
  (a) continuously measuring the electrical properties data of mastication for a first predefined period of time;
  (b) periodically determining single bites according to the data obtained in step (a) of the preliminary stage, through a time interval;
  (c) periodically storing the bites determined throughout the first period of time and the time of each bite, through a time interval;
  (d) periodically calculating the time gaps between bites, through a time interval;
  (e) providing a predetermined time duration, determining groups of sequential time gaps between bites such that each sequential time gap in each group is beneath the predetermined time duration;
  (f) adding the sequential time gaps in each group and storing the added sequential time gaps in each group;
  (g) calculating an average of the summed sequential time gaps obtained in each group to be the second period of time;
  (h) adding the number of sequential time gaps in each group;
  (i) calculating an average of the number of sequential time gaps in each group to be the threshold;
 ii. the regular stage comprises:
  (j) continuously measuring the electrical properties data of mastication of a user for a predetermined third period of time;
  (k) periodically determining single eating bites according to the data obtained in step (j) of the regular stage through a time interval;
  (l) periodically storing the bites determined throughout the third predetermined period of time, through a time interval;
  (m) periodically summing up the number of bites determined during the past second period of time, through a time interval;
  (n) periodically determining if the summed up number of step (m) of the regular stage exceeds said threshold, through a time interval; and
  (o) triggering an alert if the determining in step (n) of the regular stage is deemed to be positive.

Preferably, only the groups which have an added sequential time gaps above a predetermined threshold, are counted in the average of step (g) of the preliminary stage.

Preferably, only the groups which have added numbers of sequential time gaps above a predetermined threshold, are counted in the average of step (i) of the preliminary stage.

The present invention relates to a method for calculating eating bites of a user wherein the method comprises a preliminary stage and a regular stage wherein:
 i. the preliminary stage comprises:
  (a) continuously measuring the electrical properties data of mastication for a first predefined period of time;
  (b) periodically determining single bites according to the data obtained in step (a) of the preliminary stage, through a time interval;
  (c) periodically storing the bites determined throughout the first period of time and the time of each bite, through a time interval;
  (d) periodically calculating the time gaps between bites, through a time interval;
  (e) providing a predetermined time duration, determining groups of sequential time gaps between bites such that each sequential time gap in each group is beneath the predetermined time duration;
  (f) adding the sequential time gaps in each group and storing the added sequential time gaps in each group;
  (g) determining the group with the largest summed sequential times and determining it's summed sequential times to be the second period of time;
  (h) adding the number of sequential time gaps in each group;
  (i) determining the group with the largest summed number of sequential times and determining it's summed number of sequential times to be the predetermined threshold;
 ii. the regular stage comprises:
  (j) continuously measuring the electrical properties data of mastication of a user for a predetermined third period of time;
  (k) periodically determining single eating bites according to the data obtained in step (j) of the regular stage through a time interval;
  (l) periodically storing the bites determined throughout the third predetermined period of time, through a time interval;
  (m) periodically summing up the number of bites determined during the past second period of time, through a time interval;
  (n) periodically determining if the summed up number of step (m) of the regular stage exceeds said threshold, through a time interval; and
  (o) triggering an alert if the determining in step (n) of the regular stage is deemed to be positive.

The present invention relates to a portable bioelectric signal management system for determination of eating habits parameters of a subject in need thereof, said system comprising:
 (a) at least one electrode configured to receive an EEG and/or EMG signal;
 (b) at least one means for storing of said EEG and/or EMG signal operatively connected to said at least one electrode to transfer said signal from said electrode via at least one EEG and/or EMG channel;
 (c) at least one means for transferring of said stored signal obtained via said at least one channel, from said at least one means for storing to at least one means for processing;

wherein said means for processing of said signal is adapted to determinate said eating habits parameters of said subject, by processing said signal(s) obtained via said channel(s).

Preferably, the means for processing are configured to calculate eating bites of a user comprising:

(i) continuously measuring the electrical properties data of mastication of a user for a predetermined period of time;

(ii) periodically determining single eating bites according to the data obtained in step (i) through a time interval;

(iii) periodically storing the bites determined throughout the predetermined period of time, through a time interval;

(iv) periodically summing up all the number of bites stored, through a time interval;

(v) periodically determining if the summed up number of step (iv) exceeds a predetermined threshold, through a time interval; and (vi) triggering an alert if the determining in step (v) is deemed to be positive.

Preferably, the means for processing are configured to determine single eating bites comprising the steps of: obtaining the voltage signals of mastication;

transforming said voltage signals into frequency range signals;

obtaining the PSD of a predetermined frequency band of the frequency range signals as a function of time, through time intervals;

obtaining the PSD peaks being peaks located at maximum points of the frequency range signals in said predetermined frequency band as a function of time;

determining the amplitudes of the PSD peaks that are above a certain threshold or within a certain range, as potential bites;

measuring the gaps between said potential bites;

determining the PSD peaks between each gap as a definite bite when the following conditions are held true in relation to each measured gap:

(1) the measured gap is within a predetermined threshold range;

(2) the gap's subsequent gap is within said threshold range.

Preferably, the means for processing are configured to determine single eating bites by further comprising an additional step of filtering out noises in the frequency range.

BRIEF DESCRIPTION OF THE DRAWINGS

The present invention is illustrated by way of example in the accompanying drawings, in which similar references consistently indicate similar elements and in which.

DETAILED DESCRIPTION OF THE INVENTION

Figure 1:
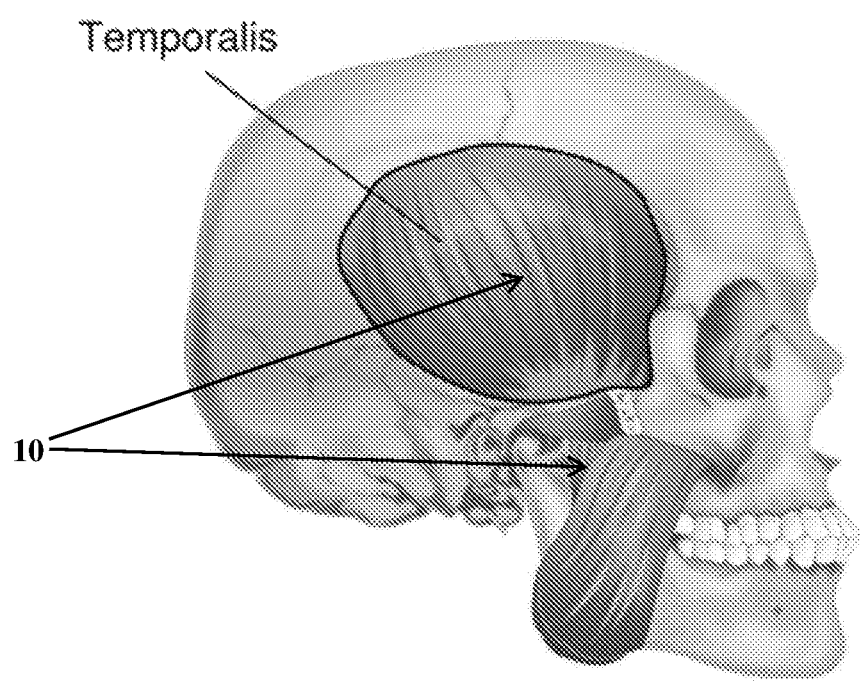
FIG. 1. illustrates mastication muscles where the electrodes may be placed.

The present invention relates to a system and method for monitoring and analyzing EEG and/or EMG signals from a user subject (head, brain) and alerting the user subject once the readings show of a deviation from a predefined threshold. The present invention enables a user to self-monitor himself in relation to the process of eating throughout the day. This self-monitoring can provide a broader perspective and awareness of the quantities and quality of food consumption during the day. Accordingly, the present invention can provide a real and clear evaluation that can lead to behavioral change regarding food consumption and nutrition.

The method of the invention relates to monitoring of the neural activity of a subject's brain performed by using electroencephalography (EEG) electrodes designed to measure the neural activity of the brain. According to another embodiment (or additionally thereto), the monitoring is of muscles activity (electrical impulses within a person's muscles) that can be measured by EMG electrodes designed to measure the electric potential generated by muscle cells when these cells are activated.

Decades of EEG practice in various medical (epilepsy, sleep) and para-medical (EEG NeuroFeedack) procedures proved the accuracy and importance of EEG as a non-invasive tool for measuring brain and muscles activity. EEG or EMG (Electromyograph) electrodes located on certain scalp areas or muscles that contract due to the eating process (e.g. chewing and swallowing), can provide signals indicative of the different aspects of the eating process according to a pre-defined class of signals.

Both of the aforementioned diagnostic tests (EEG and EMG) are performed using equipment that records the electrical activity. The measured information about the digestion and biting of food can come from both of said diagnostic tests.

According to one embodiment of the present invention, the measurements are from EEG electrodes. The measured signal reflects neuronal activity and motor artifacts generated by different aspects of food (including liquids) consumption. In this case the electrodes location is in approximate to the Muscles of mastication (e.g. temporal cortex), generally around the temporal and parietal brain areas bilateral (F7, FC5, T7 CP5, P7, F8, FC6, T8, CP6, P8). However, additional data can be obtained from other electrodes located at other locations on the head surface (e.g. over the whole surface of the head, the central and frontal facial areas) and/or on the neck. The motor artifacts in the EEG signal caused by the muscles activity related to the chewing and biting reflect different aspects of the chewing activity.

According to another embodiment of the present invention, the measurements are neural activity only gathered from EEG electrodes. The measured signal reflects neuronal activity originating from brain areas related to eating; motor brain areas (face, jaws, tongue), taste brain areas and smell brain areas. Location of the electrodes in this case will be over the relevant brain areas (Motor cortex and the somatosensory areas BA 1, 2, 3, 4).

According to another embodiment of the present invention, the measurements are from EMG electrodes. The measured electrical signal in this embodiment originates from the muscles activity related to the chewing activity. The EMG neural activity monitored is of muscles active during food intake or of muscles nearby (around the chewing related muscles). The mastication muscles, including among others—the masseter muscle and the temporalis muscle, produce a typical electro effect while contracting, that can be measured by the electrodes.

FIG. 1. illustrates mastication muscles 10 where the electrodes may be placed on or near according to certain applications, and capture their jaw related movements. The mastication muscles are responsible for adduction of the jaw.

Figure 2:
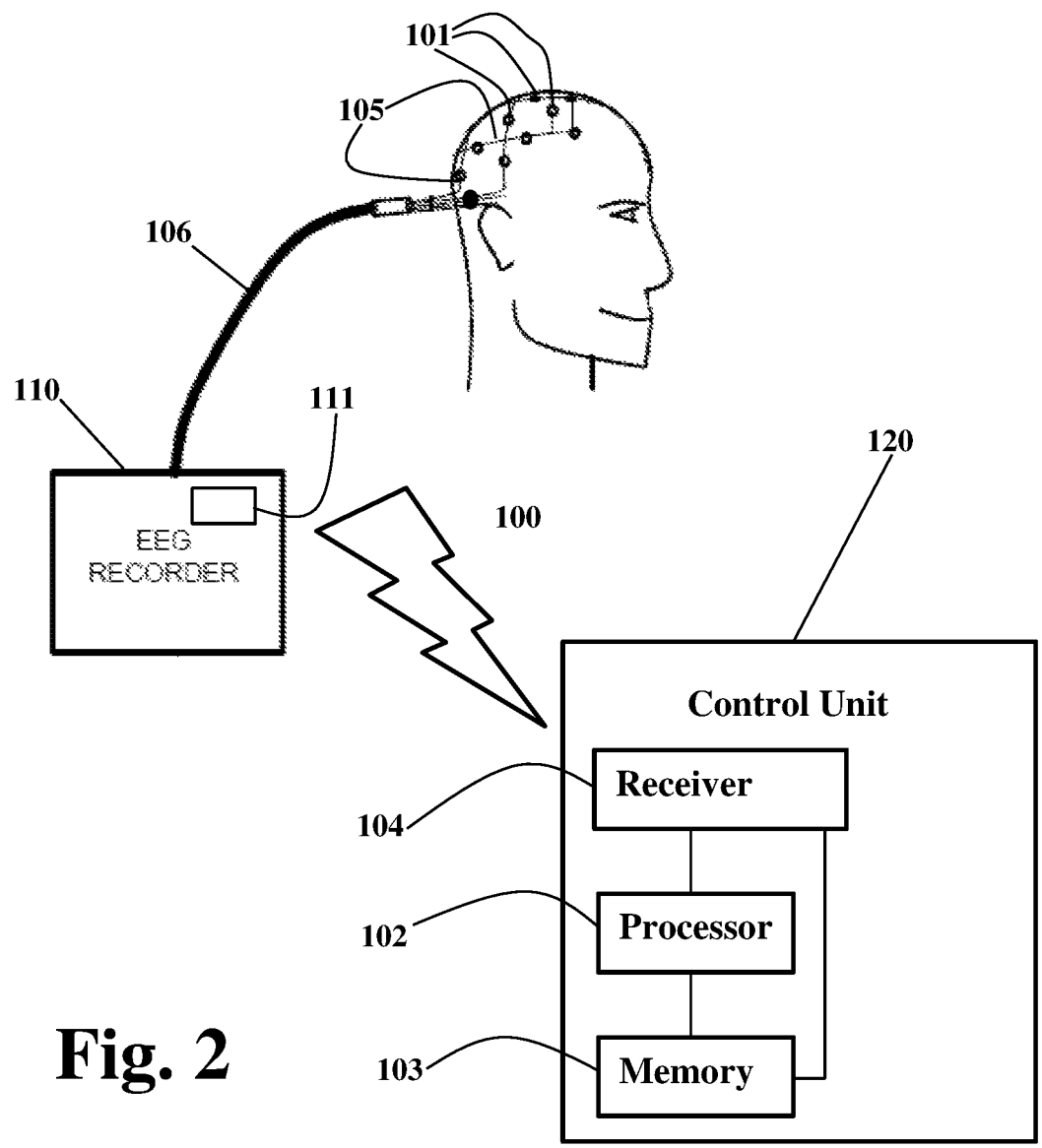
FIG. 2 shows a block diagram of personal wearable neural activity monitor system.

The present invention relates to a system for performing the continuous measurements of neural activity, especially neural muscles activity indicative of mastication of a subject user. FIG. 2 shows a block diagram of personal wearable neural activity monitor system 100 adapted to be carried by a person. The personal wearable neural activity monitor system 100 is carried by the individual continuously during daily life. System 100 relates to a portable bioelectric signal management system for determination of eating habits parameters of a subject in need thereof.

The monitor system comprises EEG and/or EMG sensors being a plurality of electrodes 101 coupled to a recorder unit 110. For the EEG embodiment, the electrodes (typically scalp electrodes) may be placed on the scalp in various measuring alignments as known in the art and the measuring can be according to various EEG methods known in the art. Typically, the EEG measures voltage fluctuations resulting from ionic current within the neurons of the brain.

Typically each electrode 101 is connected by a wire 105 to the recorder unit 110. The recorder unit may be a typical EEG/EMG recorder as known in the art. The recorder unit typically comprises a built in analog to digital converter and optionally a primary filter and can output digital signals, as known in the art in these types of recorders. According to some embodiments the recorder may include analog measurements.

Typically, the plurality of wires 105 pass through a central main cable 106. The electrodes 101 are configured to be arranged on the skin surfaces of a subject user, either on or near the scalp (for EEG) or on or about the muscles that contract (for EMG) due to the eating process.

An example of an EEG recorder and electrodes is the unit recorder system—"Avatar Portable Physiological Recorder" of Electrical Geodesics, Inc. Eugene, USA. This system also includes a set of 8-channel electrodes with sintered Ag/AgCl ring electrodes (8 EEG channels, 1 ECG channel, and 1 EOG channel and amplifier. The 8 electrodes may be attached to the head scalp with Collodion (Mavidon Medical FL USA) over the occipital, parietal and temporal areas covering the equivalent standard 10/20 placements (FT9, T7, TP9, FT10, T8, TP10).

The monitor system 100 further comprises a control unit 120. The control unit 120 comprises a processor 102 and a memory 103 electrically coupled to the processor 102. The control unit further comprises a receiver 104 electrically coupled to the processor 102 and memory 103. A commercial example of the control unit 120 is a Lenovo Yoga 2 (8 inch) tablet, manufactured by Lenovo Group Ltd, Beijing, China. This small-size tablet comprises the processor, the receiver and the memory, for gathering the data in real time. Matlab software installed on the tablet (Matlab 6.01 software, Mathworks Inc, Natick, Mass.) may be used to analyze the measured signals in real-time and produce a readable recording of the signals.

The EEG/EMG recorder 110 is configured to measure and record the continuous EEG/EMG signals and transmit the signals to transmitter 111 to which it is coupled to. Optionally the recorder unit comprises a built in transmitter 111 which transmits the signals in real time to the receiver 104. The transmitter 111 may be a transmitter that transmits wirelessly e.g. Bluetooth, RF transmission, WIFI, etc. Optionally the transmitter 111 may transmit the signals to the control unit 120 (either to the receiver 104 or to directly to the processor 102) by a wire connection. The processor 102 is configured to receive the online transmitted signals.

According to a specific embodiment the control unit 120 may be part of the recorder 110 in which case the transferring means from the recorder 110 to the control unit 120 is via internal wire coupling.

The processor 102 is configured to perform calculations, store them in the memory and use them later on. The electro data sent to the processor 102 is analyzed by the processor 102 such that when electro data representing a certain activity for a certain time exceeds a certain threshold the user is alerted. The processor 102 is configured to calculate a baseline level of activity and store it in the memory 103. The processor 102 is configured to calculate a current state indicating a number of mastication actions made during a certain time range and compare it to the baseline level of activity stored in the memory 103. The processor 102 is configured to calculate the deviation between the baseline level and the current state and determine if it exceeds a predefined threshold and if positive trigger an alert. More specific actions of the processor 102 will be explained hereinbelow in relation to the present invention method.

The system 100 comprises alerting means to alert the user once the processor 102 triggers an alert. The alerting means may be earphones, headphones, speakers, etc., electrically coupled to the control unit 120 or the alerting signal can be wirelessly transmitted. The wireless alert comprises the processor 102 being coupled to a transmitter (not shown) that can send an alerting signal via wireless means (e.g. Bluetooth RF transmission, WIFI, etc.) to the earphones (which comprise an appropriate receiver to receive the signal and thereafter activate a noise alert, as known in the art). Optionally the receiver 104 can be a transceiver that can also transmit the alert signal. Other means of alerting include sending a message from the processor 102 directly to a smart phone or to an email (in which case the control unit 120 comprises suitable cellular communication means or suitable internet communication means as known in the art). Optionally, other recorded collected data such as feedback signals indicative of the chewing of a user may also be sent to a smart phone or email in the same manner.

The speakers/earphones are preferably mounted on ear hooks configured to hook onto the ears of a subject user. The processing unit 120 may be mounted on a neck belt configured to hook onto the neck of a subject user.

Optionally, the system (or portions thereof) may be hidden, e.g. the electrodes may be covered by the individual's hair, etc.

The alert may be the speakers/earphones sounding a tone for a certain period of time. The audio level is adjusted according to the user's request.

The present invention method comprises the use of the control unit 120 (and its components) for executing the general controlling of system 100. The present invention method comprises the use of the processor 102 for executing calculations, transformations (e.g. Fourier), comparisons, determinations, triggering etc. Optionally, the whole control unit may be part of or integrated with the recording unit.

Preferably, the present invention method comprises a first stage to determine a user baseline. EEG or EMG signals are measured during a certain time period and being indicative of a subject's baseline activity. The EEG measurements are collected from a plurality of electrodes on the user's scalp.

The EMG measurements are collected from a plurality of electrodes on or near the mastication muscles. It should be understood that the alerting method may be applied by using EEG brain signals obtained from electrodes from the scalp, or by using EMG muscle electric signals obtained from electrodes from the mastication muscles. The analyses of the signals may be performed for either EEG or EMG signals. Optionally, signals may be obtained from both and analyzed accordingly thereafter.

The total number of single chews and each chew being on a time scale, can be measured throughout the day. The terms relating to eating bites, e.g. "chews", "bites", mastication and "mastication action" are used herein interchangeably. Furthermore, during drinking (for example), the jaw muscles are activated in a similar manner as during eating. The upper and the lower jaws engage closer and depart further from one another during both eating and drinking and thus create a similar effect on the EEG (or EMG) signal. Therefore, the term "eating bites" as described herein may also refer to other forms of actions related to the jaw (during food/drink intake), e.g. sipping, sucking, licking, etc. Accordingly, a single "bite" as described herein may also refer to a single drinking sip, a single suck action, a single lick, etc.

The initial measuring forming the baseline activity of a user is a type of average/normal state which indicates the limit allowed to occur prior to triggering an alert. Several baseline/average values are calculated during the initial time of using the device. One baseline value represents time of no mastication. This value may be used for calculating the amplitude of the user's mastication. Averages of daily chewing values and/or the chewing during a meal values (quantity and quality) can be calculated for periodic data, which can be used to determine a threshold, especially if the user consumes the maximal food appropriate for his required diet for that day/meal, which can be most efficient for a baseline threshold. If the user knows that he ate too much the day of the initial measuring, the measurements of that day may be discarded and the initial process set for another day). Optionally, the initial baseline may be determined by averages of data obtained from two or more measuring days.

According to one embodiment, the threshold total number of chews a day is determined in the initial process such that if the total number of chews in the regular use mode exceeds the threshold determined in the initial process, an alert is triggered by the processor. Thus the maximum chews allowed a day is determined by the initial process. Optionally, the threshold number of maximum chews allowed a day may be predefined by the user (e.g. according to a specific health plan). In any case, once the number of chews exceeds the daily threshold the user is alerted.

According to another embodiment, a threshold number of maximal chews per meal are determined in the initial process such that if the total number of chews per meal in the regular use mode exceeds the threshold per meal determined in the initial process, an alert is triggered by the processor. Thus the maximum chews allowed per meal are determined by the initial process. Optionally, the threshold number of maximum chews allowed per meal may be predefined by the user (e.g. according to a specific health plan). In any case, once the number of chews exceeds the threshold per meal, the user is alerted.

A meal may be identified according to a predefined number of bites during a certain time and will be explained hereinbelow.

A plurality of alerting methods may be applied simultaneously. For example, the method may comprise alerting the user if he exceeds a maximal number of bites aloud per day, or if he exceeds a maximal number of bites allowed per meal.

The method of the invention comprises performing EEG/EMG temporal measurements of a user during daily activity and generating EEG/EMG temporal data. The present invention method comprises real time computation of the recorded data first in order to identify a baseline level of activity and then to measure such activity in real time wherein the measured data is continually processed and compared to the stored baseline level. According to the method of the present invention, deviation from the baseline or from other predefined values will result in alerting the user of such occurrence, thereby, allowing the user to return to a desired state.

The present invention method relates to a method for acquiring and analyzing EEG and EMG data continuously from a subject user and providing the user with a feedback concerning his current eating state.

Full Day Alert Method

According to an embodiment of the present invention the method comprises alerting a user if he exceeds an eating state, said method comprises the steps of:

(a) continuously measuring (and optionally storing) the electrical properties data of mastication for a predetermined period of time;

(b) periodically determining single bites according to the data obtained in step (a) through a time interval (the time interval preferably being between 10 and 300 seconds);

(c) periodically storing the bites determined throughout the predetermined period of time, through a time interval (the time interval preferably being between 10 and 300 seconds);

(d) periodically summing up all the number of bites stored, through a time interval (the time interval preferably being between 10 and 300 seconds);

(e) periodically determining if the summed up number of step (d) exceeds a predetermined threshold, through a time interval (the time interval preferably being between 10 and 300 seconds); and (f) triggering an alert if the determining in step (e) is deemed to be positive.

The present invention method may further comprise determining the initial baseline parameter, wherein the initial baseline parameter is the predetermined threshold (e.g. number of bites per day), which will be used in the actual analysis and alerting process.

The predetermined period of time (for either the initial baseline process or for the actual analysis and alerting process) may be the time the user is awake, e.g. from 6 in the morning till 11 at night, or it might be 24 hours, or other desired times according to a specific health plan. According to this embodiment, the predetermined threshold (e.g. number of bites per day) to be used in the analysis and alerting process is determined during a baseline recordation process as follows:

(a) continuously measuring (and optionally storing) the electrical properties data of mastication for a predetermined period of time (determined by the user);

(b) periodically determining single bites according to the data obtained in step (a) through a time interval (the time interval preferably being between 10 and 300 seconds);

(c) periodically storing the bites determined throughout the predetermined period of time, through a time interval (the time interval preferably being between 10 and 300 seconds);

(d) summing up all the number of bites stored during the predetermined period of time (e.g. at the end of the predetermined period of time) wherein the sum is the "predetermined threshold" to be used in the analysis and alerting process.

Meal Alert Method

According to another embodiment of the present invention the method comprises alerting a user if he exceeds an eating state (bites per meal), said method comprises the steps of:

(a) continuously measuring (and optionally storing) the electrical properties data of mastication for a first predefined period of time;

(b) periodically determining single bites according to the data obtained in step (a) through a time interval (the time interval preferably being between 10 and 300 seconds);

(c) periodically storing the bites determined throughout the first period of time and the time of each bite, through a time interval (the time interval preferably being between 10 and 300 seconds);

(d) provided a second predetermined period of time (meal duration), periodically summing up the number of bites determined during the past second predetermined period of time (from the second predetermined period of time ago until the current time, e.g. during the last 7 minutes) through a time interval (the time interval preferably being between 300 and 1800 seconds);

(e) periodically determining if the summed up number of step (d) exceeds a predetermined threshold, through a time interval (the time interval preferably being between 300 and 1800 seconds); and (f) triggering an alert if the determining in step (e) is deemed to be positive.

Optionally, step (d) may be carried out only at certain predetermined periods of time during the day, for example, during breakfast time (e.g. 7:30-8:30), during lunch (e.g. 12:30-13:30) and during dinner (e.g. 18:30-19:30). Preferably the time durations are according to the user's individualized health plan.

Optionally the periodically summing up the number of bites in step (d) occurs every predetermined number of bites counted, wherein the method further comprises counting each bite and summing up the number of bites during the past second predetermined period of time, and doing so every predetermined number of bites counted, e.g. every 20 bites.

The present invention method preferably further comprises determining the initial baseline parameters, i.e. the predetermined threshold (e.g. number of bites per meal) and the second predetermined period of time (meal duration) which will be used in the actual analysis and alerting process. The first predefined period of time may be similar to the predefined period of time explained in relation to the Full Day Alert Method hereinabove (furthermore it should be noted that alternatively, the predetermined threshold and/or the second predetermined period of time to be used in the analysis and alerting process, may be determined by the user, e.g. according to a specific health plan).

The initial baseline first predetermined threshold (e.g. number of bites per meal) and the second predetermined period of time (meal duration) to be used in the analysis and alerting process is determined during a baseline recordation process as follows:

(a) continuously measuring (and optionally storing) the electrical properties data of mastication for a first predefined period of time;

(b) periodically determining single bites according to the data obtained in step (a) through a time interval (the time interval preferably being between 10 and 300 seconds);

(c) periodically storing the bites determined throughout the first period of time and the time of each bite, through a time interval (the time interval preferably being between 10 and 300 seconds);

(d) periodically calculating the time gaps between bites through a time interval (the time interval preferably being between 10 and 300 seconds);

(e) providing a predetermined time duration (being a maximal time gap (duration) between adjacent bites during a meal), determining groups of sequential time gaps between bites such that each sequential time gap in each group is beneath the predetermined time duration;

(f) adding the sequential time gaps in each group and storing the added sequential time gaps in each group;

(g) calculating an average of the summed sequential time gaps obtained in each group to be the second predetermined period of time (meal duration) to be used in the analysis and alerting process;

(h) adding the number of sequential time gaps in each group;

(i) calculating an average of the number of sequential time gaps in each group to be the first predetermined threshold (e.g. number of bites per meal) to be used in the analysis and alerting process.

Optionally, if the added sequential time gaps in each group is beneath a certain threshold, not counting it in the average of step (g). In other words only if the added sequential time gaps in each group is above a certain threshold—counting it in the average of step (g).

Optionally, if the added number of sequential time gaps in each group is beneath a certain threshold, not counting it in the average of step (i). In other words only if the added number of sequential time gaps in each group is above a certain threshold—counting it in the average of step (i).

Optionally, the method calculation of time gaps may not necessarily be between two adjacent bites, but rather between every other bite, every 4 bites, every 10 bites, or every predetermined number of bites, mutatis mutandis.

According to a specific embodiment of the present invention, the longest meal properties (i.e. properties of the longest meal eaten in the day) in the initial baseline process will be used for the analysis and alerting process, in which the method comprises steps (a)-(f) as they appear hereinabove with the following steps.

(g1) determining the group with the largest summed sequential times and determining it's summed sequential times to be the second predetermined period of time (meal duration) to be used in the analysis and alerting process;

(h1) adding the number of sequential times in each group;

(i1) determining the group with the largest summed number of sequential times and determining it's summed number of sequential times to be the predetermined threshold (e.g. number of bites per meal) to be used in the analysis and alerting process.

According to an embodiment of the present invention, the full day alert method (according to any one of its variations) may be used in conjunction with the meal alert method (according to any one of its variations) mutatis mutandis. Accordingly, exceeding a predetermined of number of bites per meal and also exceeding a maximal predetermined number of bites per day, will trigger an alert. Also the initiation baseline process according to both methods (according to any one of their variations) may be used in conjunction, mutatis mutandis.

The following aspects hereinbelow may be used in either one of the methods mentioned hereinabove (unless specifically stated otherwise).

Preferably, the electrical properties data of mastication may be obtained from EEG electrodes on the scalp and thus the electrical properties are neuronal activity responsible to the different aspects of the chewing activity.

Preferably, the electrical properties data of mastication may be obtained from EMG electrodes and thus the electrical properties are the measured electrical signals originating from the muscles activity related to the chewing activity.

Preferably, The electrical properties data of mastication may be the voltage signal (e.g. measured in my or in µv) between two pair electrodes or the average of a plurality of electrode pairs or the voltage signal averaging of an array of electrodes placed either on the scalp (for EEG) or on or about the mastication muscles (for EMG). According to one aspect, if the measurement reaches a given value (or if a certain analysis on the measurement reached a given value) it is considered a bite.

The analysis of the electric signal measured may be carried out as follows. Mathematical algorithms calculate and identify the repetition of bites i.e. mechanical repetition of the jaw, while the process of eating takes place. Unlike other face-related muscles activity (laugh, speech, yawn, smile, etc.), during mastication the jaw is activated in a repetitive and continues way which creates a specific finger print differ from the non-mastication activities. This repetitive jaw activity is the base for the bites quantity measurements of the invention (which includes filtering out signals that are not within the frequency range of the repetitive bites).

The determination of the chewing activity from the ongoing EEG or EMG signal may be performed by a set of sequential algorithms applied (by the processor), aimed to identify repetitive signals having amplitudes above a certain level.

According to a preferred embodiment, the method "measuring the electrical properties data of mastication and determining single bites" comprises:

(a) obtaining the signals measured by the EEG/EMG electrodes (e.g. voltage signals as a function of time) and transforming them into the frequency range (e.g. Fourier transform—FFT, stockwell, Hilbert);

(b) filtering out noises;

(c) obtaining only the signals from the required frequency range for repetitive mastication action (bites).

Transformation

The Raw EEG/EMG signals are usually sampled at a frequency between 250 Hz and 500 Hz, preferably 500 Hz. Then the signal is transformed into the frequency range (e.g. by FFT, stockwell, Hilbert). The transform may be according to a time resolution between 1/250 sec and 1/500 sec, preferably 1/500 sec. The transform may be according to a frequency resolution between 0.5 Hz and 2 Hz, preferably 2 Hz.

Noise Filtering

The noise filtering may comprise filtering out frequencies related to Power line artifacts. This could be implemented by using a band-stop filter for a certain appropriate range in which the signals of these bands (and harmonics) are extracted and not counted in further analysis. An example of a frequency range affected by power line filtering is in the range of 50 Hz or 60 Hz. An example of such an appropriate range is the range of (49.9, 50.1) Hz and its harmonics (around 100 Hz, around 150 Hz., etc.).

The noise filtering may comprise filtering out frequencies related artifacts induced by motor movements. The user motion is a prominent source of artifact in EEG time series. Additional noise appliers may be muscle movement (when activated by unrelated behavior such as talking, laughing, yawning, etc.).

Optionally, Noise related to motor artifacts is defined as being a predefined number more than the median readings and replaced with the median readings. For example, if the readings are more than 30 times the median it is replaced with the median data. The present application method may comprise the use of applications stored in the control unit (such as Matlab software) that use statistics application and evaluate the degree of S/N (signal-to-noise) ratio and reject minutes with low level of S/N. Thus only minute segments with high value of S/N are further analyzed.

Figure 3:
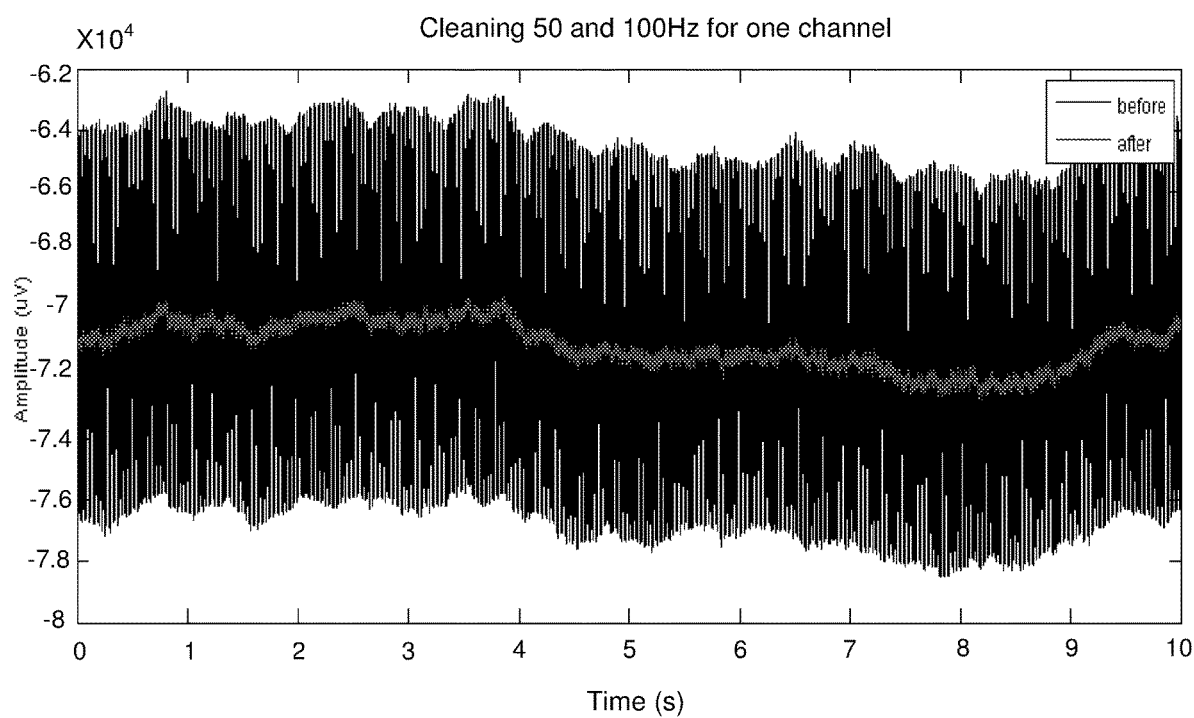
FIG. 3 shows an example of a graph of the measured signal amplitudes (in μv) as a function of time noise filtered out.

FIG. 3 shows an example of a graph of the measured signal amplitudes (in µv) as a function of time, wherein the signals with frequency bands near 50 H and 100 Hz are filtered out.

Figure 4:
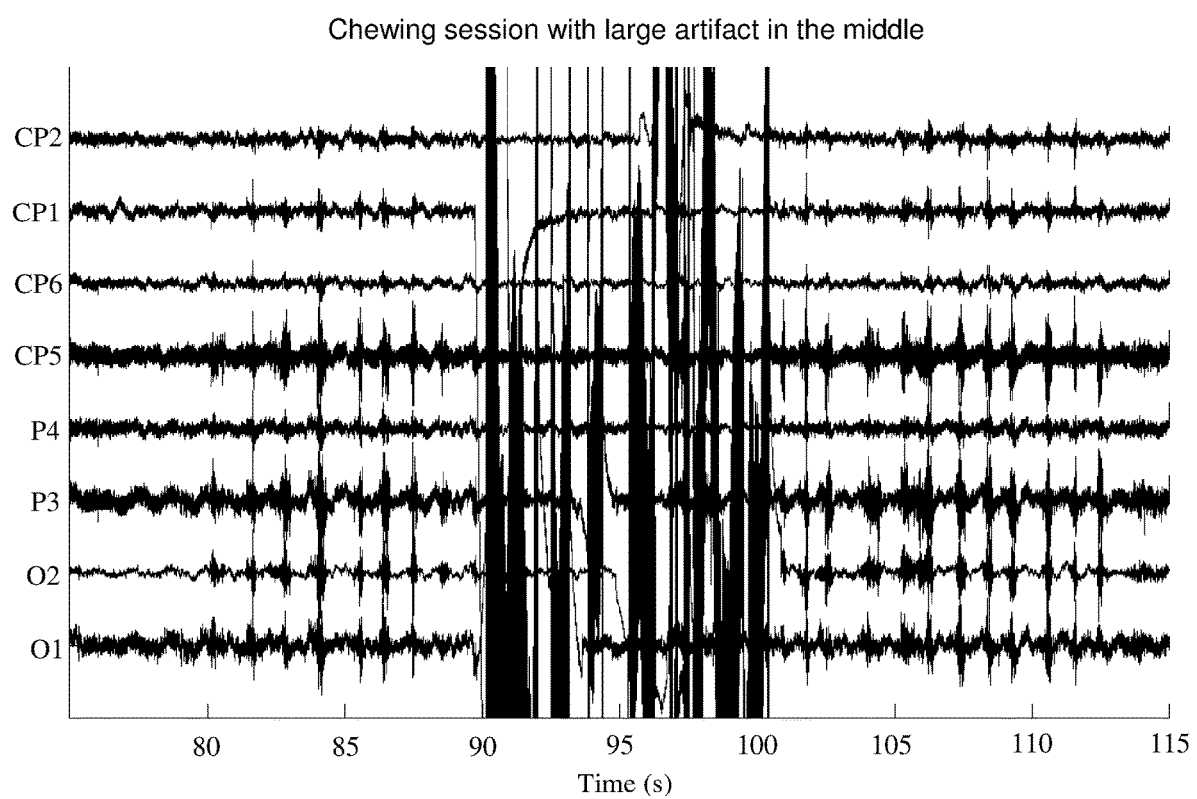
FIG. 4 shows a graph of a signal with and without the motor artifacts.
Figure 5:
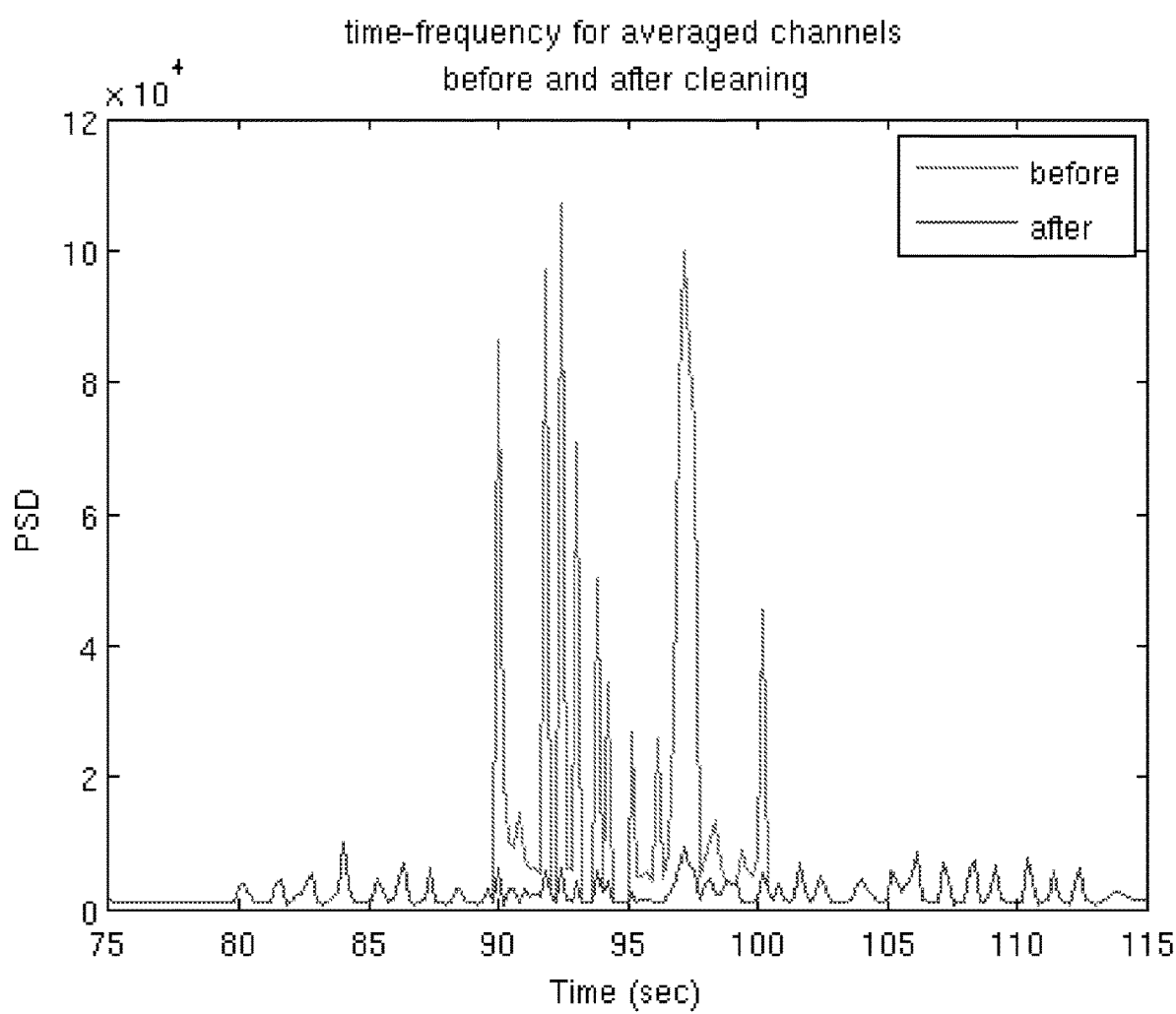
FIG. 5. Shows a PSD graph of signals before and after filtering out the motor artifacts.

FIG. 4 shows a graph of the signal (EEG Amplitude (µV) as function of time) with and without the motor artifacts (with the large artifacts in the middle). The significant noise (more than 30 times the median, not related to mastication) is replaced with a median signal. FIG. 5 Shows a PSD graph of signals before and after filtering out the motor artifacts.

Required Band

The transformation to the frequency domain obtains the calculation of the electrode signals averaged Power Spectral Density function (PSD) which represents the strength of the variations (energy) as a function of frequency over time. The process comprises obtaining the PSD of the required frequency band for the bites detection (after filtering out noise as mentioned). The required frequency band that corresponds to mastication during eating is usually the Gamma band (which typically provides efficient results indicative of bites). The Gamma band instantaneous power is extracted from the time-frequency transform as the average power across the relevant bands. Specifically, using the Stockwell transform the EEG signal is transformed into separate distinguished frequencies (whose number depends on the frequency resolution or frequency sampling rate) with continues amplitude values for each of the frequencies over time. The Gamma range is averaged over the 60-160 HZ resulting with continuous and instantaneous Gamma band values over time (with ~0.1 s resolution). The Gamma band may be according to frequencies between 30 HZ and 160 HZ, preferably 60-160 HZ. The peaks in the PSD required frequency band (over time) are detected and the interval between them (gaps) is measured. For every few seconds (or every predetermined period of time, e.g. 10 seconds) in the required frequency band—the number of peaks, their averaged amplitude and the number of gaps are calculated and stored.

More particularly, all the peaks in the required frequency range (Gamma band) of the 10 second measured (or predetermined period of time) are measured. According to a preferred embodiment, the determination of bites relies on two main parameters amplitudes of peaks and gap length (repetitive and similar gaps between peaks occurring one after the other).

First, the amplitudes of peaks are measured. If the peaks are above a certain threshold or within a certain range (e.g. between 3500 and 20000 uV^2/Hz) than the peak is considered a potential bite. Then the time gaps between the potential bites are measured. If the gaps are within a certain threshold range (e.g. between 0.3 to 1.4 s) and if two or more consecutive gaps are within the threshold range, then the peaks between the consecutive gaps are considered actual detected bites (definite bites) for further method calculations as described hereinabove.

Optionally, another manner of calculation such that the consecutive gaps determine actual bites of the peaks at their edges, is if 2 consecutive gaps have up to a certain percent (e.g. 20%) difference between their lengths.

The magnitude of the amplitude of the detected bites, their place on the time scale, and also the gaps between the detected bites, are stored and used for the method calculations as described hereinabove.

Figure 6:
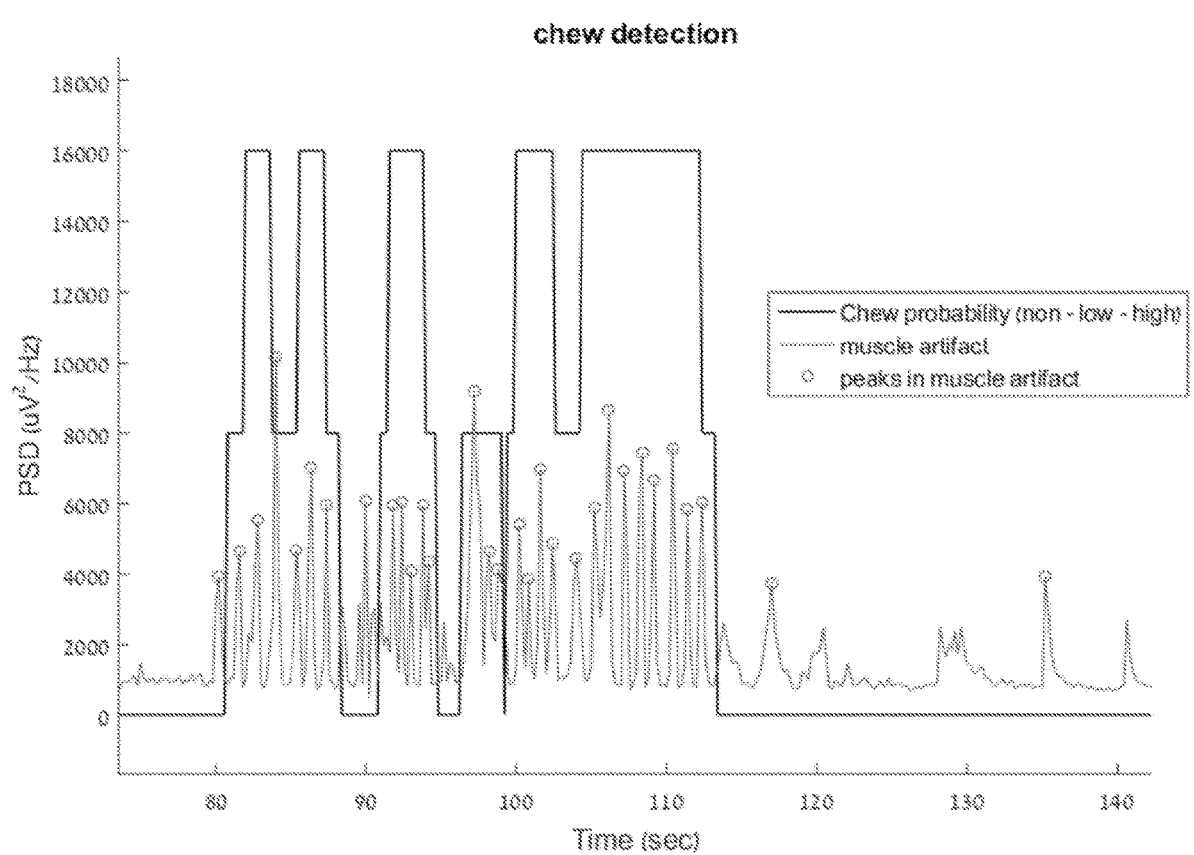
FIGS. 6-7 show a graph with the PSD peak amplitudes on a time scale.
Figure 7:
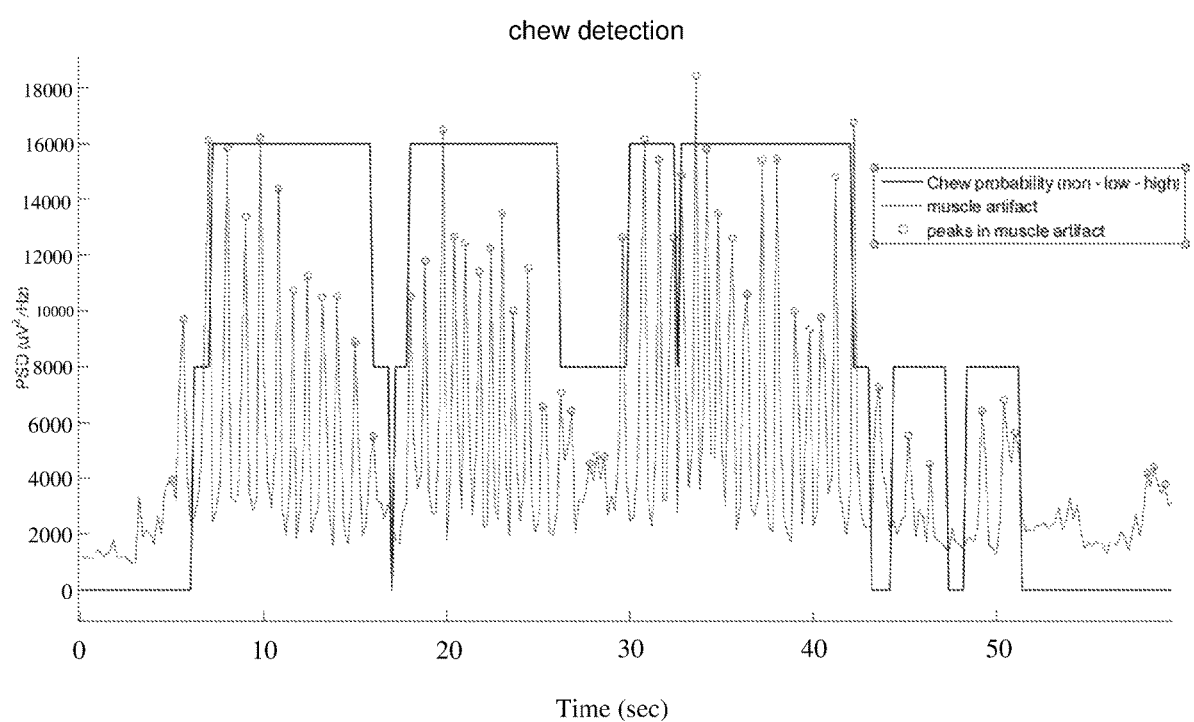

Chewing activity is defined as to repetition of peaks with quiet time between them. The method comprises detecting peaks in the continuous gamma band signal described above (preferably having an amplitude of peaks between 3500 and 20000 uV^2/Hz) and then calculating the gaps between peaks (bites). Another indication of the chewing is when there are two peaks near to each other with quiet time in between. High probability of chewing when there is another bite before or after. The number of repetitive peaks, gaps between them, and the height of the peaks amplitude are saved and compared to predefined values for determining bites. FIGS. 6-7 show a graph with the PSD peak amplitudes on a time scale. The areas of dense peaks on the graphs indicate eating time windows. In the example of FIG. 6, a bite peak is determined in the range of between 3500 and 20000 uV^2/Hz.

Preferably, the calculation of the bites is according to an EEG/EMG protocol related equation which includes the electrodes location, the band which the signals are measured and their value. The method comprises determining a single bite as being a PSD peak within a predetermined level range.

An example for detecting bites of the jaw for EEG electrodes includes measurement in the Gamma band in the range of 60-160 Hz, recorded from the bilateral temporal electrodes or temporo/parietal electrodes FT9, T7 and TP9, FT10, T8 and TP10. The gamma power is then extracted from the time-frequency transform as the average power across the relevant bands.

According to a specific embodiment of the present invention, the present invention comprises identification of the unique mastication activity related to various types of foods e.g. vegetables, cheese, fruits, nuts etc., or drinking e.g. water, beer or licking ice-cream.

Based on numerous characteristics of the electrical reflection of the repetitive jaw bites (amplitude, delay between bites, shape of the signal and more) the present invention is capable of distinguishing between the different types of foods being chewed.

Figure 8:
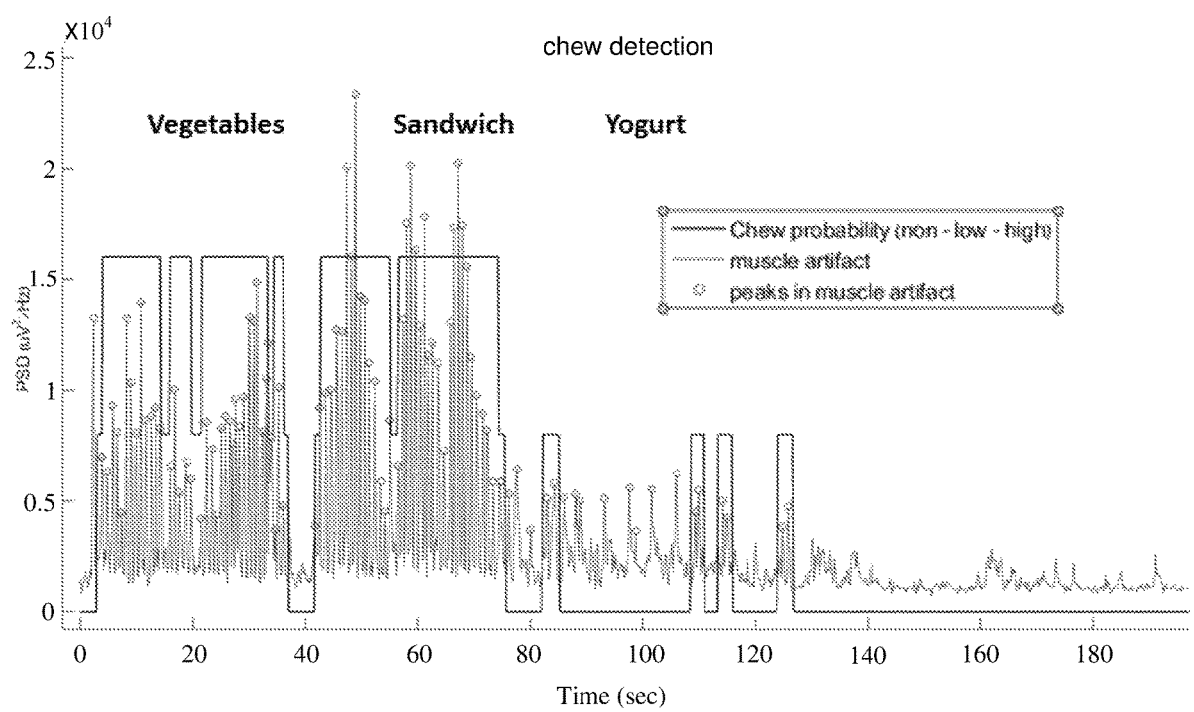
FIG. 8 shows a graph with the PSD peak amplitudes on a time scale according to different food types.

Following the spectral analysis (e.g. Fast Furrier transform) and the identification of the muscle activity as chewing period, a quality analysis may be made. Quality analysis relies upon the relation between muscle activity and neuro-electrical response; the stronger the muscle contraction and the higher the number of activated muscles, the higher the recorded voltage amplitude will be. The quality analysis involves calculation of the electrodes averaged Power Spectral Density function (PSD) which shows the strength of the variations (energy) as a function of frequency (e.g. 60-160 HZ) over a period of time, and comparing this average to pre-defined categories of amplitudes ranges. These pre-defined categories represent the different types of food being chewed. Different types of foods produce bites with different amplitudes. Amplitudes of vegetables are in the range of 0.75-1.5*10^4 (uV^2/Hz); sandwiches in the range of 1-2*10^4 (uV^2/Hz), and less solid foods like eating yogurt produce smaller amplitude in the range of 0.25-0.5*10^4 (uV^2/Hz). FIG. 8 shows a distribution of the 60-160 HZ energy level (PSD, uV^2/Hz on a time scale) according to the different food types. This distribution enables the categorization of energy levels to the different food types. In this example, the difference between solid (vegetables) solid (sandwich) and soft (yogurt) is visible. Information about the quality of the food being eaten over the day may hold important insights for the user regarding eating habits. The quality analysis measurements may be stored for daily reports.

According to a preferred embodiment, the method comprises determining the type of food eaten according to the amplitude of the PSD peaks of the definite bites, wherein a type of food is determined in case a predetermined number of consecutive definite bites are within a predefined range.

Specifically, the continuous monitoring is conducted for a time period of from about 1 day to a few months, without being limited to, preferably for periods not short then 5 weeks. According to the method of invention the choice of relevant EEG signals (electrodes and bands) is predefined and made according to a user's specific needs, such as, for example, over eating or over drinking.

When the alert is triggered the user is notified about the deviation (e.g. by the earphones, e.g. by a 10 seconds soft sound), thereby, allowing the user to control his eating consumption for the near future, e.g. to rethink about his immediate food consumption choices. Each user has his individual manner to return to normal state. One example would be, in the case of exceeding number of bites per day, to reduce the number of calories until the end of the day.

According to an embodiment of the present invention the user may view the number of bites determined already during a specific day/meal, or the number of bites left before triggering an alarm. In that case the processor is coupled to display means (such as a display screen) and the user may view upon demand. This case is especially useful for a user to adapt his diet for the remaining day/meal according to the readings.

According to one embodiment of the invention, the present invention may also be used for the opposite purpose. More specifically, the present invention is also useful for continuous monitoring of eating-related EEG/EMG signals to notify the user about undesired long periods of not eating or not drinking. Periods of not eating could result in blood glucose drops below normal levels for people at risk. This notification can assist the user to immediately self-regulate his sugar level in order to regain normal levels of glucose.

According to this embodiment if a predetermined time passes with a number of bites below a certain threshold, then the alert is triggered, mutatis mutandis. The initiation process of this embodiment is also carried out mutatis mutandis.

The present invention provides an advantageous real-time feedback, wherein the user is able to regulate his eating choices in order to control, modify and subsequently improve conscious eating habits.

Optional operation: The data may be downloaded every predetermined period of time (e.g. every night) to a device (e.g. smartphone, tablet, etc.) that comprises an application that uses the data to produce continuous daily food consumption reports, trends and alerts. Optionally, the data may be downloaded every predetermined period of time to a device the comprises an application that uses the data to contact necessary personnel in case of data exceeding a predefined threshold (or e.g. repeated data values that crossed the threshold) indicating deviation from normal brain activity related to the predefined measures.

The long-term continuous measurements of neural and muscles activity, while comparing to a baseline data or predefined data, are useful for revealing special features in the EEG/EMG and for producing specific insight into the user's eating profile over time.

Optionally, only part of the data is stored for further off-line analysis as needed. Data for storage includes: Baseline values and daily eating times. In the case of feedback values that cross the threshold all the daily samples may be stored for future off-line analysis.

Optionally, upon agreement of the user, his neuroelectrical mastication data will be transferred to a global database that will gather information from multi-communities about chewing and eating habits for the purpose of increasing the knowledge about eating habits and improve the definition of chewing thresholds and averages across ages, genders and cultures.

A WORKING EXAMPLE

In the current experiment EEG electrodes were used to measure motor artifacts and the present invention system was used to quantify the motor artifacts in the obtained signals related to the chewing activity. These motor artifacts have special characteristic (60-160 HZ, repetitive higher amplitudes) which distinguish them from other types of noise (speech, facial expression, etc. . . . ). In the current experiment bites were able to be counted. Defining the types of food (soft, hard) was also possible based on the repetitive peak amplitudes, level of the artifact amplitude and space between the peaks.

A plurality of EEG electrodes were placed on the temporal lobe (FT9, T7 and TP9, FT10, T8 and TP10), as well as, Bias electrode and a reference electrode. The bias electrode is used as a means to counter the common-mode interference in an EEG system as a result of power lines and other sources, including fluorescent lights. EEG signals were recorded and stored in a processor (in tablet model Lenovo Yoga 8" comprising Windows 8.1 with Matlab version R2014a installed).

The EEG signals were continuously obtained and stored. Every 2 minutes the following calculation took place:

- a. An fft function (Stockwale) was applied to the signals, enabling to filter out the harmonics of the power line artifacts (50 HZ, 100 Hz . . . ) and to identify the continuous 60 HZ-160 HZ gamma band amplitudes.
- b. A function for removal of large motor artifacts not related to eating was applied on the gamma band signal extracting all amplitudes above 30 times the median value.
- c. Next, A series of characteristics and statistics analysis was run over the gamma signal resulting with numbers reflecting various aspects of the eating process (determination of number of bites, what was eaten (soft or hard food, liquid, etc.).

The data was stored and evaluated in order to determine for example if the user exceeded the pre-defined number of bites per meal or per day etc. When the user exceeded the pre-defined values—an alert was triggered and a soft tone noise was sounded in an earphone to the user in order to notify the user of the exceeding.

While some of the embodiments of the invention have been described by way of illustration, it will be apparent that the invention can be carried into practice with many modifications, variations and adaptations, and with the use of numerous equivalents or alternative solutions that are within the scope of a person skilled in the art, without departing from the spirit of the invention, or the scope of the claims.

The invention claimed is:

1. A method for calculating eating bites of a user wherein the method comprises a preliminary stage and a regular stage wherein:
   i. the preliminary stage comprises:
   - (a) continuously measuring electrical properties data of mastication for a first predefined period of time;
   - (b) periodically determining single bites according to data obtained in (a) of the preliminary stage, through a time interval;
   - (c) periodically storing bites determined throughout a first period of time and a time of each bite, through a time interval;
   - (d) periodically calculating time gaps between bites, through a time interval;
   - (e) providing a predetermined time duration, determining groups of sequential time gaps between bites such that each sequential time gap in each group is beneath a predetermined time duration;
   - (f) adding the sequential time gaps in each group and storing added sequential time gaps in each group;
   - (g) calculating an average of summed sequential time gaps obtained in each group to be the second period of time;
   - (h) adding a number of sequential time gaps in each group; and
   - (i) calculating an average of the number of sequential time gaps in each group to be the threshold; and
   ii. the regular stage comprises:
   - (j) continuously measuring electrical properties data of mastication of a user for a predetermined third period of time;
   - (k) periodically determining single eating bites according to data obtained in (j) of the regular stage through a time interval;
   - (l) periodically storing bites determined throughout the third predetermined period of time, through a time interval;
   - (m) periodically summing up bites determined during a past second period of time, through a time interval;
   - (n) periodically determining if summed up number of (m) of the regular stage exceeds said threshold, through a time interval; and
   - (o) triggering an alert if the determining in (n) of the regular stage is deemed to be positive.

2. The method according to claim 1, wherein only the groups which have an added sequential time gaps above a predetermined threshold, are counted in the average of (g) of the preliminary stage.

3. The method according to claim 1, wherein only the groups which have added numbers of sequential time gaps above a predetermined threshold, are counted in the average of (i) of the preliminary stage.

4. A method for calculating eating bites of a user wherein the method comprises a preliminary stage and a regular stage wherein:
   i. the preliminary stage comprises:
   - (a) continuously measuring electrical properties data of mastication for a first predefined period of time;
   - (b) periodically determining single bites according to the data obtained in (a) of the preliminary stage, through a time interval;
   - (c) periodically storing bites determined throughout a first period of time and a time of each bite, through a time interval;

(d) periodically calculating the time gaps between bites, through a time interval;
(e) providing a predetermined time duration, determining groups of sequential time gaps between bites such that each sequential time gap in each group is beneath a predetermined time duration;
(f) adding the sequential time gaps in each group and storing added sequential time gaps in each group;
(g) determining the group with the a largest summed sequential times and determining its summed sequential times to be a second period of time;
(h) adding the number of sequential time gaps in each group; and
(i) determining the group with the a largest summed number of sequential times and determining its summed number of sequential times to be a the predetermined threshold; and ii. the regular stage comprises:
(j) continuously measuring the electrical properties data of mastication of a user for a predetermined third period of time;
(k) periodically determining single eating bites according to the data obtained in step (j) of the regular stage through a time interval;
(l) periodically storing bites determined throughout the third predetermined period of time, through a time interval;
(m) periodically summing up a number of bites determined during a past second period of time, through a time interval;
(n) periodically determining if the summed up number of step (m) of the regular stage exceeds said threshold, through a time interval; and
(o) triggering an alert if the determining in step (n) of the regular stage is deemed to be positive.

* * * * *